United States Patent [19]
Abend et al.

[11] Patent Number: 5,961,966
[45] Date of Patent: Oct. 5, 1999

[54] QUATERNARY FATTY DIESTERS OF HYDROXYPROPYL DIETHANOL AMINE

[75] Inventors: Phillip G. Abend, Fort Lee; Abel G. Pereira, Belleville; Frank Hess, Fords, all of N.J.

[73] Assignee: Croda, Inc., Parsippany, N.J.

[21] Appl. No.: 08/987,315

[22] Filed: Dec. 9, 1997

Related U.S. Application Data

[60] Provisional application No. 60/032,138, Dec. 9, 1996.

[51] Int. Cl.⁶ ........................................................ A61K 7/06
[52] U.S. Cl. ...................... 424/70.28; 510/130; 510/276; 510/515; 554/110
[58] Field of Search ........................ 554/110; 424/70.28; 510/518, 276, 130

[56] References Cited

U.S. PATENT DOCUMENTS

| | | |
|---|---|---|
| 5,180,508 | 1/1993 | Birkhan et al. . |
| 5,364,542 | 11/1994 | Birkhan et al. . |
| 5,409,621 | 4/1995 | Ellis et al. ................................ 252/8.8 |

*Primary Examiner*—Deborah D Carr
*Attorney, Agent, or Firm*—Lerner, David, Littenberg, Krumholz & Mentlik, LLP

[57] ABSTRACT

A quaternary fatty diester of 2-hydroxypropyl diethanol amine and aqueous dispersions thereof useful as fabric softening products, laundering products, household cleaning products and personal hair and skin care products. Methods for softening textiles, fabrics or laundry articles with the quaternary fatty diesters of the present invention are also disclosed.

18 Claims, No Drawings

QUATERNARY FATTY DIESTERS OF HYDROXYPROPYL DIETHANOL AMINE

CROSS-REFERENCE TO RELATED APPLICATION

The present application claims priority benefit of U.S. Provisional Application Ser. No. 60/032,138 filed Dec. 9, 1996, the disclosure of which is incorporated herein by reference.

BACKGROUND OF THE INVENTION

Fatty diester quaternary salts have been used in fabric softeners for a few years now. Their advantage over other fatty quaternary salts is that they exhibit rapid biodegradability relative to conventional fabric softening agents be they fatty alkyl or fatty alkyl amido types. However, even though fatty ester quaternary salts have been shown to be more biodegradable than their fatty alkyl or fatty alkylamido analogues, they are also more difficult to formulate, including previously patented triethanolamine fatty ester quaternary salts. A fatty ester quaternary salt exhibiting a lower handling temperature enabling it to be stored at lower temperatures and transferred from one vessel to another with greater ease would also be desired.

INVENTION SUMMARY

These needs are met by the present invention. In accordance with one embodiment of the present invention, there is provided a quaternary fatty diester of 2-hydroxypropyl diethanol amine having the structure of Formula I:

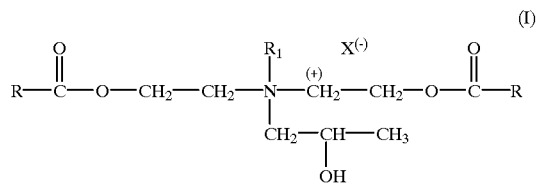

wherein each R is independently selected from aliphatic hydrocarbon groups having from about 8 to about 24 carbon atoms; $R_1$ is independently selected from hydrogen, benzyl groups and one to four carbon atom alkyl groups; and X is an anion.

The present invention provides fatty diester quaternary salts that are water dispersible yet confer an exceptional hand feel to fabrics treated therewith that has long been desired for use in laundering and in personal care products. Therefore, in accordance with another embodiment of the present invention, aqueous dispersions of the fatty diester quaternary salts of the present invention are provided, which may be additionally formulated with conventional laundering and personal skin and hair care active ingredients.

Textiles and fabrics may be softened utilizing aqueous dispersions of the fatty diester quaternary salts of the present invention. Therefore, in accordance with yet another embodiment of the present invention, a method of softening textiles or fabrics is provided which includes the step of contacting textiles or fabrics with a water bath containing a dispersion of between about 0.05 and about 0.50 weight percent of the fatty diester quaternary salts of the present invention.

DETAILED DESCRIPTION OF THE PREFERRED EMBODIMENT

The fabric softening agents of the present invention are quaternary salts of fatty diesters of hydroxypropyl diethanol amine. Fatty acids suitable for use in the present invention may contain from 8 to 24, and preferably from 16 to 18, carbon atoms. The fatty acids may be saturated, unsaturated or polyunsaturated, Hydroxyl-substituted castor oil-type fatty acids may also be employed. The fatty acids may also be branched. Iso-branched fatty acids are particularly desirable because they impart liquidity to the compounds of the present invention.

Examples of such fatty acids include caprylic, capric, decanoic, undecanoic, lauric, dodecanoic, tridecanoic, myristic, tetradecanoic, pentadecanoic, hexadecanoic, palmitic, heptadecanoic, stearic, oleic, linoleic, linolenic, nonadecanoic, eicosanoic, behenic, tetracosanoic and the like. The preferred fatty acids or the mixtures thereof may be derived from tallow, soy bean, rape seed or coconut oil. Tall oil fatty acids are also exemplary of a naturally occurring mixture of acids suitable for use in the present invention.

For purposes of the present invention "fatty acids" are defined as including, in addition to the fatty acid itself, the alkyl esters thereof and the naturally occurring glyceride esters. In the methods of the present invention, the glyceride ester form of the fatty acid splits in the course of the initial condensation of the fatty acid moiety and the hydroxypropyl diethanol amine, and the glycerol by-product can be readily removed from the reaction mixture by conventional means. Because the naturally occurring glyceride form of the above-listed animal and vegetable derived fatty acids are more economical than the free acids or the monoesters, it is particularly preferred to use these fatty acids in this form.

The initial condensation of the fatty acid and hydroxypropyl diethanol amine forms a diester, which is obtained by heating a reaction mixture containing the reactants to a temperature between about 120° C. and about 160° C., and preferably between about 135° C. and about 150° C. A nitrogen sparge is preferably used throughout the condensation.

The hydroxypropyl diethanol amine is reacted with the fatty acid in a ratio of between about 0.8 and about 1.2 moles of the hydroxypropyl diethanol amine to two moles of the fatty acid. When the triglyceride form of the fatty acid is used, two-thirds of a mole thereof is employed in order to provide the two moles of fatty acid for combining with the hydroxypropyl diethanol amine in the ratio described.

Quaternization of the fatty diesters can be carried out in a conventional manner. In particular, because the diester condensation is performed at elevated temperatures, the reaction mixture is allowed to cool, preferably below 80° C., and a concentrated solution of the fatty diester is formed in an inert solvent. The temperature to which the reaction mixture is cooled will depend upon the volatility of the solvent and the quaternizing agent. The cooling is preferably accomplished by the addition of a lower temperature inert solvent to the reaction mixture.

The quaternization reaction is carried out by adding from about one mole to a slight molar excess of a quaternizing agent to a concentrated solution of the fatty diester. Temperatures suitable for this reaction range from about room temperature to about 70° C., and preferably between about 40° C. and about 60° C. Reaction temperature will depend upon the volatility characteristics of the inert solvent and can be readily determined by those of ordinary skill in the art without undue experimentation.

The quaternizing agents suitable for use in the inventive method are also essentially conventional. Suitable quaternizing agents include the lower alkyl chlorides and bromides, e.g., methyl chloride; the di-lower alkyl sulfates;

ethylene chlorohydrin; epichlorohydrin and benzyl chloride or iodide. Preferred quaternizing agents include methyl chloride, dimethyl and diethyl sulfate and benzyl chloride. Optimum reaction times are obtained with dimethyl sulfate, or with combinations of one or more of the above-listed quaternizing agents with dimethyl sulfate.

Although the compounds of this invention are particularly useful in fabric softening applications, other important uses are indicated. For example, the quaternized products of the present invention are also useful in laundry detergents and other household cleaning products, personal care products for the hair and skin, softening additives for use in paper manufacturing, antistatic agents for paper, fabric, polish and the like, and emulsifiers for oil and water emulsions, including bituminous or asphaltic materials.

The quaternary salts of the present invention possess unique water dispersability. Aqueous dispersions of the quaternary salts are novel, and may be additionally formulated with conventional laundering, household cleaning products and personal skin and hair care active ingredients. The quaternary salts of the present invention, and aqueous dispersions thereof, are useful in the formulation of lotions, skin moisturizers, cleansing creams, cream rinses and hair conditioners, sunscreens, hair dressing preparations, bath additives, laundry detergent products, household cleaning detergent products, depilatories, permanent waving solutions, hair relaxers, and the like.

Aqueous dispersions of the quaternary salts of the present invention may include one or more active ingredients such as sunscreens, moisturizers, film forming polymers, non-ionic detergents, thickening agents, emulsifiers other than nonionic detergents, conditioning agents, depilatories, permanent waving agents, hair relaxers, substantive proteins, and the like. A second, prior art, quaternary ammonium salt can optionally be included.

The fabric softening, laundering, household cleaning product and personal hair and skin care compositions of the present invention, in addition to including the aqueous dispersion of the quaternary salts of the present invention, one or more active ingredients and the optional prior art quaternary salts, may also include coloring agents, fragrances, optical brighteners, dispersants, sanitizers, and the like. These additional components may be added in various amounts as is well known to those of ordinary skill in the art. A typical fabric softening composition in accordance with the present invention will include from about 3 to about 30 percent by weight of one of the quaternary salts of the present invention in aqueous dispersion, and preferably from about 5 to about 25 percent by weight of the composition.

Textiles and fabrics may be softened utilizing aqueous dispersions of the quaternary salts of the present invention by the method of the present invention in which the fabrics and textiles are contacted with the aqueous dispersions. In a typical ten pound wash load, the concentration of the quaternary salt is diluted to between about 0.05 and about 0.50 weight percent of the wash load.

Typical laundry detergent compositions in accordance with the present invention include the quaternary salts of the present invention and range from about four to about eight percent by weight of the composition, and preferably from about five to about seven percent by weight of the composition in aqueous dispersion. A nonionic detergent compound is present in an amount from about 20 to about 40 percent by weight of the composition, and preferably from about 28 to about 32 percent by weight. Triethanolamine, ethanol, fragrances, optical brighteners and coloring agents may also be present.

Personal skin and hair care products in accordance with the present invention include the quaternary salts of the present invention in aqueous dispersion in a range of from about one to about eight percent by weight of the composition, and preferably from about two to about five percent by weight. One or more active ingredients may be present in an amount from about 0.5 to about five percent by weight of the composition, and preferably from about two to about four percent by weight of the composition.

The fabric softening, laundering, household cleaning products and personal hair and skin care products of the present invention are formulated utilizing techniques that are well-known in the art. Typically, the ingredients are combined with mixing and the addition of heat if necessary until a uniform, homogeneous dispersion is formed. The water-soluble and water-insoluble ingredients are mixed together separately and combined with suitable emulsifying ingredients, to form an emulsion.

The following non-limiting examples set forth hereinbelow illustrate certain aspects of the present invention. They are not to be considered limiting as to the scope and nature of the present invention.

EXAMPLES

| PHYSICAL PROPERTY COMPARISON | | |
|---|---|---|
| | HPD Ester | TEA Ester |
| Congealing Point | 48° C. | 63° C. |
| Temp. to clear liquid | 60° C. | 80° C. |

HPD Ester = Distearyl Hydroxypropyl Diethanolamine Ester Quanternary Salt
TEA Ester = Distearyl Triethanolamine Ester Quaternary Salt The compounds of the present invention have a much lower temperature at which they are a clear liquid and a much lower congealing point. Although unexpected, this is a highly desirable property, because the compounds can be stored at lower temperatures than their TEA analogues. This results in less time and energy being needed to melt the compounds and less energy to keep them molten. The lower storage temperatures can also result in improved compound stability during extended storage periods. In addition, the low congealing point relative to the TEA analogues means less problems transferring the compounds from the storage vessel to the compounding vessel. In a production setting, these types of compounds are usually pumped through transfer lines which need to be pre-warmed in order to prevent the product from solidifying in the line during transfer. The compounds of the present invention offer a significant advantage over their TEA analogues due to their significantly lower congealing points.

PERFORMANCE COMPARISONS

The above-mentioned quaternary salts have various applications. One important application is in the production of fabric softener bases. These fabric softener bases generally consist of the following:
1) Fatty Quaternary Salt
2) Water
3) Calcium Chloride
4) Fragrance The fabric softeners bases are mainly dispersions of fatty quaternary salts in water with activities varying as desired from <5 percent to >20 percent. The fabric softener bases must have certain desired characteristics such as low viscosity, uniform particle size and good water dispersability. Frequently during the production of the fabric softener bases, the whole dispersion will thicken and a processing aid such as calcium chloride is added to break down the viscosity. Excessive use of calcium chloride, however, is detrimental to the performance of the product and in most cases the thinning effect has a limit no matter how much calcium chloride is used.

In addition to the previously described physical advantages over TEA-based ester quaternary salts, the present invention also exhibits better performance in the production of fabric softener bases.

In the production of an 8 percent active fabric softener base, the present invention compares to a TEA analogue as follows:

|  | HPD Ester | TEA Ester |
|---|---|---|
| Initial Viscosity | 120 cps | 410 cps |
| + 0.25% CaCl$_2$ | 60 cps | 560 cps |
| Water dispersability (initial) | Fair | Poor |
| + 0.25% CaCl$_2$ | Excellent | Poor |
| Particle Size |  |  |
| 2–5 microns | 90% | 2% |
| 10–20 microns | 5% | 90% |
| 20–40 microns | 5% | 8% |

As can be seen, the HPD ester quaternary salt had lower initial viscosities compared to the TEA analogue and responded well to the addition of CaCl$_2$ while the TEA analogue actually increased in viscosity. In addition, the water dispersability of HPD ester quaternary salt final fabric softener base was excellent compared to the TEA analogue. Water dispersability of the fabric softener base is a key property. If the base does not disperse in water very well, it will not deposit evenly on the fabric. Uneven deposition can yield potential staining problems as well as poor softening at the less treated sites. Large particles may also fail to deposit altogether and be discharged in the drain cycle of the washer. This results in inferior softening and economics.

Examination of the dispersions under the microscope revealed that the HPD ester quaternary salt fabric softener base consisted of a much smaller particle size compared to the TEA analogue, 90 percent in the 2–5 micron region vs. 90 percent in the 10–20 micron region. The lower particle size is believed to be a factor in the overall water dispersability of the base.

All of the above improved properties of the HPD ester quaternary salt over its TEA analogue is believed to be due to the secondary alcohol group present in the hydroxylpropyl diethanolamine. The secondary hydroxy group is less reactive than the other two primary groups present in the molecule. It is believed that the lower reactivity of this group results in less triester formation as compared to the TEA. Triester quaternary salts would have a higher melting point and would be less dispersible than the diester.

The properties of the present invention also indicate its in cationic preparations for use on hair and skin.

| Cationic Lotion | % W/W |
|---|---|
| Distearoylethyl Hydroxypropylmonium Methosulfate | 1.25 |
| Crodafos CES | 4.50 |
| Crodamol PMP (PPG-2 Myristyl Ether Propionate) | 2.50 |
| Mineral Oil | 5.00 |
| Water | 86.75 |

Crodafos CES, an emulsifying wax available from Croda, Inc. of Parsippany, N.J., is a blend of cetearyl alcohol, dicetyl phosphate and diceteth 10 phosphate. Crodamol PMP is also available from Croda, Inc.

Combine all ingredients and stir while heating to 75° C. Continue stirring while allowing to cool to 25° C. and fill off.

| Hair Conditioner | % W/W |
|---|---|
| Distearoylethyl Hydroxypropylmonium Methosulfate | 1.25 |
| Crodafos CES | 3.50 |
| Cetearyl Alcohol | 1.50 |
| Crodamol MM (Myristyl Myristate) | 1.00 |
| Water | 92.75 |

Crodamol MM is also available from Croda, Inc.

Combine all ingredients and stir while heating to 75° C. Continue stirring while allowing to cool to 25° C. and fill off.

EXAMPLE 1

PREPARATION OF HYDROXYPROPYL DIETHANOL AMINE

To a stirred pressure vessel fitted with nitrogen, vacuum, heat and cooling, and a pressurized propylene oxide feed were added 630 grams (6.0 mole equivalents) of diethanolamine. The vessel was purged three times with nitrogen and heated to 75° C. Propylene oxide addition was started and continued until 355 grams (6.11 mole equivalents) were added. Cooling and heating were used as needed to maintain the temperature between 75° C. and 80° C. Pressure was kept below 45 PSI.

The final product was a clear, colorless liquid with a tertiary amine content >98 percent.

EXAMPLE 2

PREPARATION OF DIESTER OF HYDROXYPROPYL DIETHANOL AMINE

To a 2000 ml 4 neck, round bottom flask, were charged 730.1 grams (2.645 mole equivs.) of stearic acid and 228.46 grams (1.37 mole equivs.) of hydroxypropyl diethanol amine, the mixture was reacted at 140–200° C. until an acid value of >10 mg KOH and a base value of 77–84 mg KOH is reached.

EXAMPLE 3

PREPARATION OF DIESTERQUAT OF HYDROXYPROPYL DIETHANOL AMINE

To a 2000 ml 4 neck, round bottom flask, were charged 866 grams (1.287 mole equivs) of the ester of Example 2. The product was heated until molten and 180.6 grams of propylene glycol was added as solvent. The temperature was adjusted to between 55–80° C. and 157.3 grams (1.249 mole equivs) of dimethyl sulfate were added. The product was allowed to stir at 55–80° C. until a base value of <5 mg KOH were reached. The cationic activity at this point was 83.6 percent.

An esterquat for comparison was also made from triethanolamine using the same mole ratios and conditions as described in Examples 2 and 3.

EXAMPLE 4

PREPARATION OF BEHENIC DIESTERQUAT OF HYDROXYPROPYL DIETHANOL AMINE

Following the procedure of Example 2, 652.24 g (1.93 mole) of behenic acid and 166.7 g (1 mole) of hydroxypropyl diethanol amine were reacted at 170° C. until the acid value reached a value of 3.43 mg and a base value of 70.9 mg. 791.2 g (1 mole) of the behenate diester amine was quaternized with 113.4 g (0.9 mole) of dimethyl sulfate in 159.7 g of propylene glycol following the method of Example 3. The base value was 5.9 mg and cationic activity was 78.6 percent.

EXAMPLE 5

PREPARATION OF LAURIC DIESTERQUAT OF HYDROXYPROPYL DIETHANOL AMINE

The procedure of Example 2 was used for the esterification of hydroxypropyl diethanol amine with lauric acid. 396.62 g (1.93 mole) of Emery 626 and 166.7 (1.0 mole) of hydroxyethyl hydroxypropyl diethanol amine were reacted at 170° C. until the acid value reached 3.15 mg and the base value 105.9 mg.

529.7 g (1.0 mole) of the dilaurate ester amine was quaternized with sulfate in 113.49 g of propylene glycol following the method of Example 3. The base value was 8.0 mg and the cationic active matter was 79.2 percent. This product was a pale yellow liquid.

As will be readily appreciated, numerous variations and combinations of the features set forth above can be utilized without departing from the present invention as set forth in the claims. Such variations are not regarded as a departure from the spirit and scope of the invention, and all such variations are intended to be included within the scope of the following claims.

What is claimed is:

1. A quaternary fatty diester of 2-hydroxypropyl diethanol amine.

2. A diester according to claim 1, having the structure:

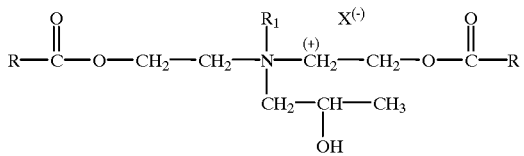

wherein each R is independently selected from the group consisting of aliphatic hydrocarbon groups having from about 8 to about 24 carbon atoms; $R_1$ is independently selected from the group consisting of hydrogen, benzyl groups and 1 to 4 carbon atom alkyl groups; and X is an anion.

3. The diester of claim 2, wherein each R is independently selected from the group consisting of aliphatic hydrocarbon groups having from about 16 to 18 carbon atoms.

4. The diester of claim 2, wherein both R groups are the same and are selected from the group consisting of stearic, behenic and lauric groups, $R_1$ is a methyl group and X is a sulfate anion.

5. An aqueous dispersion of the fatty diester quaternary salt of claim 1.

6. The aqueous dispersion of claim 5, further comprising one or more active ingredients selected from the group consisting of sunscreens, moisturizers, film-forming polymers, nonionic detergents, thickening agents, emulsifiers other than nonionic detergents, conditioning agents, depilatories, permanent waving agents, hair relaxers, substantive proteins and quaternary ammonium salts other than said quaternary fatty diester of 2-hydroxypropyl diethanolamine amine.

7. A fabric softening composition comprising the aqueous dispersion of claim 6, wherein said diester is present in an amount between about 3 and about 30 percent by weight, and optionally including one or more ingredients selected from the group consisting of quaternary ammonium salts other than said 2-hydroxypropyl diethanol amine, coloring agents, fragrances, optical brighteners, dispersants and sanitizers.

8. The fabric softening composition of claim 7, wherein said diester is present in said aqueous dispersion at a level of between about 5 and about 25 percent by weight.

9. A laundry detergent or household cleaning composition comprising the aqueous dispersion of claim 6, wherein said diester is present in an amount between about 4 and about 8 percent by weight, further comprising a nonionic detergent compound in an amount between about 20 and about 40 percent by weight and optionally further comprising one or more ingredients selected from the group consisting of triethanolamine, ethanol, fragrances, optical brighteners and colors.

10. The laundry detergent or household cleaning composition of claim 9, wherein said diester is present in said aqueous dispersion at a level between about 5 and about 7 percent by weight and said nonionic detergent compound is present in an amount between about 28 and about 32 percent by weight.

11. A personal skin or hair care product comprising the aqueous dispersion of claim 6, wherein said diester is present in an amount between about 1 and about 8 percent by weight and said one or more active ingredients are present in an amount between about 0.5 and about 5 percent by weight.

12. The personal skin or hair care product of claim 10, wherein said diester is present in said aqueous dispersion in an amount between about 2 and about 5 percent by weight and said one or more active ingredients are present in an amount between about 2 and about 4 percent by weight.

13. A method of softening textiles, fabrics or laundry articles comprising contacting said textiles, fabrics or laundry articles with a water bath comprising a dispersion of between about 0.05 and about 0.50 weight percent of a quaternary fatty diester of 2-hydroxypropyl diethanol amine.

14. The method of claim 13, wherein said fatty diester has the structure:

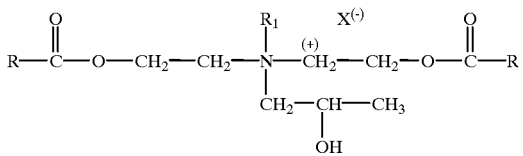

wherein each R is independently selected from the group consisting of aliphatic hydrocarbon groups having from about 8 to about 24 carbon atoms; $R_1$ is independently selected from the group consisting of hydrogen, benzyl groups and 1 to 4 carbon atom alkyl groups; and X is an anion.

15. The method of claim 14, wherein each R is independently selected from the group consisting of aliphatic hydrocarbon groups having from about 16 to 18 carbon atoms.

16. The method of claim 15, wherein both R groups are the same and are selected from the group consisting of stearic, behenic and lauric groups, $R_1$ is a methyl group and X is a sulfate anion.

17. The method of claim 13, wherein said water bath further comprises one or more ingredients selected from the group consisting of nonionic detergents, quaternary salts other than said quaternary fatty diester of 2-hydroxypropyl diethanol amine, coloring agents, fragrances, optical brighteners, dispersants and sanitizers.

18. Distearoylethyl 2-hydroxypropylmonium methosulfate.

* * * * *